United States Patent [19]

Weber

[11] Patent Number: 5,338,192

[45] Date of Patent: Aug. 16, 1994

[54] DENTAL FLASK EXPANDER AND METHOD OF USE

[76] Inventor: Joseph C. Weber, 6039 Ashway Ct., Indianapolis, Ind. 46224

[21] Appl. No.: 48,418

[22] Filed: Apr. 14, 1993

[51] Int. Cl.⁵ ............................................. A61C 19/00
[52] U.S. Cl. ........................................ 433/34; 249/54; 425/180
[58] Field of Search .................... 433/6, 34, 35, 36; 249/54; 425/175, 180

[56] References Cited

U.S. PATENT DOCUMENTS

| | | | |
|---|---|---|---|
| 258,858 | 5/1882 | Locke | 425/180 |
| 2,378,633 | 6/1945 | House | 425/180 |
| 2,440,910 | 5/1948 | Opotow | 425/180 |
| 2,457,114 | 12/1948 | Amenta | 264/18 |
| 2,471,205 | 5/1949 | Fagan | 425/180 |
| 2,491,147 | 12/1949 | Zahn | 156/61 |
| 2,574,593 | 11/1951 | Scharfe | 425/180 |
| 2,712,158 | 7/1955 | Villa | 425/180 |
| 3,316,640 | 5/1967 | Kesling | 433/6 |
| 3,635,630 | 1/1972 | Greene | 425/175 |
| 3,663,141 | 5/1972 | Alain et al. | 425/175 |

Primary Examiner—John J. Wilson
Attorney, Agent, or Firm—H. John Barnett

[57] ABSTRACT

An expander for a three-part, Hanau dental flask to add vertical height to the flask when the total height of the wax model of a prosthesis and mold material exceeds the normal height of the flask. The flask expander requires no alteration or modification of the standard dental flask, and sandwiches in between the existing flask base and body or between the flask body and lid.

8 Claims, 2 Drawing Sheets

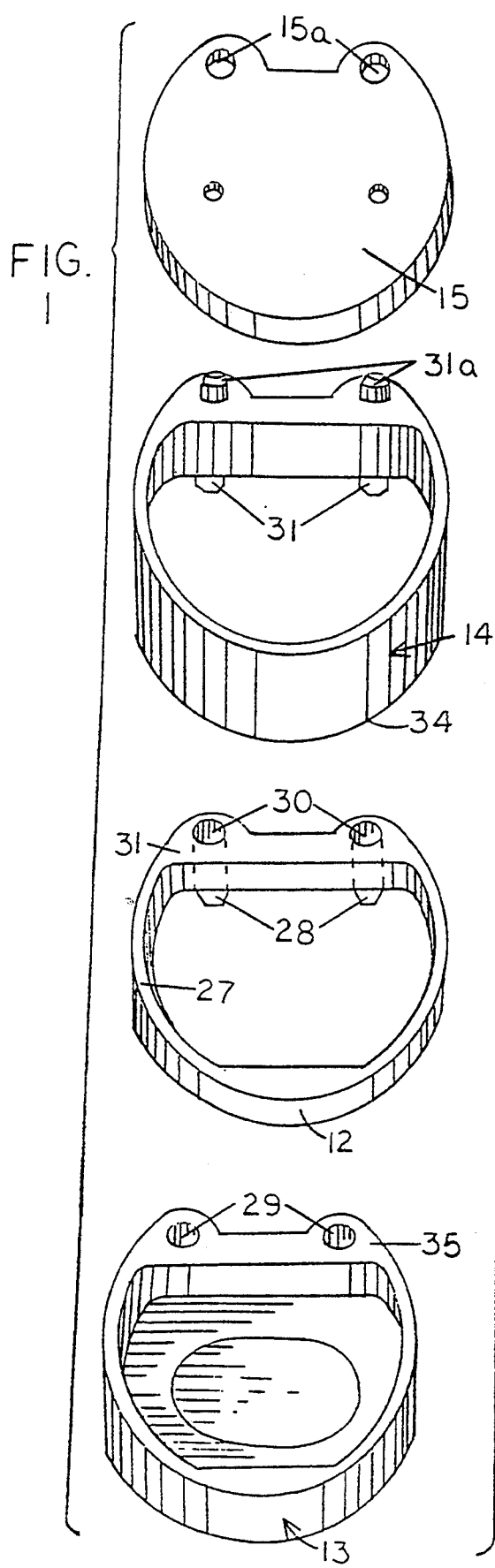
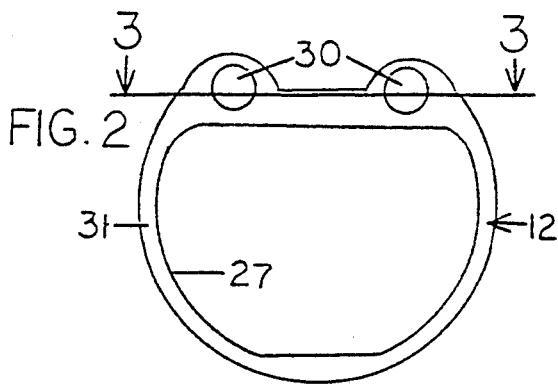
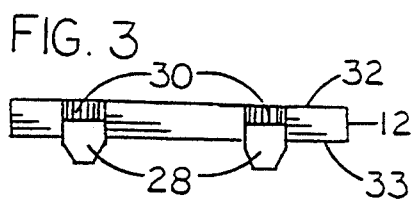
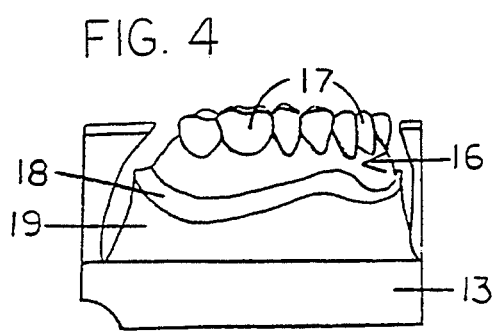
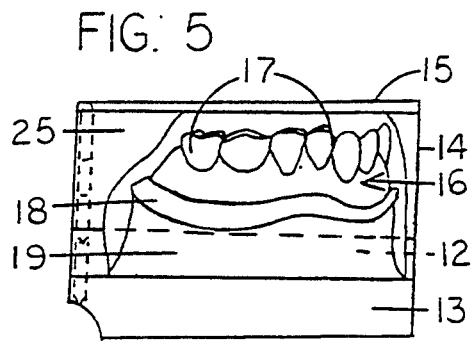

DENTAL FLASK EXPANDER AND METHOD OF USE

BACKGROUND OF THE INVENTION

1. Field of the Invention

This invention pertains to the custom manufacture of dental and maxillo-facial prostheses utilizing a lost wax molding process and metal flasks for containing the materials during the process. The invention is a particularly useful improvement to the Hanau flask.

2. Description of the Related Art

Hanau flasks have been widely used in the manufacture of dental prostheses for about sixty years. The Hanau flask has a base, a body and a lid which fit together to define an easily removable container for dental prosthesis molding materials.

Patents relating to the molding of dental prostheses include the following:

| U.S. Pat. No. | Inventor | Date |
| --- | --- | --- |
| 2,378,633 | House | 1945 |
| 2,440,910 | Opotow | 1948 |
| 2,457,114 | Amenta | 1948 |
| 2,471,205 | Fagan | 1949 |
| 2,491,147 | Zahn | 1949 |
| 2,712,158 | Villa | 1955 |
| 3,635,630 | Greene | 1972. |
| 3,663,141 | Clenet et al | 1972 |
| 4,119,292 | Haker | 1978. |

House's patent describes a dental flask which includes U-shaped fillers 12 and 16 to facilitate removal of the dentures from the investment, and to adapt the flask to the making of various sizes of lower dentures. Opotow's flask has a C-shaped intermediate section with an open side, which is closed by a flange which extends down from the cover section. This design is to facilitate banking, and would not allow for increased height.

Amenta's patent describes the use of methyl methacrylate for making dental prostheses. A two-part flask is shown.

The Fagan patent describes a four-part dental flask that can only be used with all four parts. Fagan's lid also has a depending rear wall extending down from the lid, and an upwardly extending rear wall integral with the base. There are two intermediate body sections which complete the flask. Fagan's design is not intended to add height to his flask.

Zahn relates to the method of setting synthetic resin teeth in the denture base. Zahn's flask includes a base, a two-part body, a lid and spacer blocks. The bottom spacer block is integral with the base. Villa's two-part body is described having a continuous taper (Col 2, lines 69-72, Col 3, lines 1-3). A flask expander was not contemplated by Villa because it would distort the taper between Villa's two-part body section and create a ridge in the mold.

Greene's patent is directed to plastic inserts which fit within the flask members and which facilitate rapid curing of the plastic denture in a microwave oven. The outer flask comprises three parts: a lower flask member 20; an upper flask member 22; and a top flask member 34. The plastic inserts 52 and 54 are the actual mold container, and they do not include an expander.

Clenet et al describe a method for molding prostheses articles in which the two mold halves are stationary and firmly engaged. The flask member 10 is open on top and at one end and does not provide an enclosure for the mold. The size of the flask cavity is adjustable by means of a threaded rod 50. The rod 50 has a plastic clamping member 52 which engages the back of the model 40. This flask is entirely different from the Hanau type flask. Haker describes a mould which has removable retaining elements connected to it for holding the working model in the mould. Haker has no description of a flask.

Henry La Fuente et al describe a Hanau flask in which the body member has been cut into two sections to decrease the incidence of stone fracture which sometimes occurs using a 3-piece mold. See: La Fuente, et al, Modified denture flask for three-piece ear molds *Jnl Prosthetic Dentistry* 41:453 Apr. 1979.

None of the above references disclose a dental flask expander which may be placed on top of the base of the flask under the flask body when the mold is too high for the flask body. Use of the flask expander avoids a tedious extra step of grinding down the bottom of the mold to make it fit in the standard flask.

SUMMARY OF THE INVENTION

This invention is directed to an expander for a three-part, Hanau dental flask used to mold dental and maxillo-facial prostheses. The expander is used to add vertical height to the flask when the total height of the wax model of the prosthesis and mold material will exceed the normal height of the body section of a conventional Hanau dental flask.

During the molding process, sometimes it is discovered that the top of the wax model and the mold material will be too high for the lid of the flask. In such cases, the flask expander is put in position between the base and the body of the flask to gain the extra height required so that the flask can be closed around the wax model and the mold material to complete the molding process.

Use of the flask expander eliminates the extra labor otherwise required to grind down the base of the model until it fits in the conventional flask. When such grinding is done, it modifies the position marks (guide marks) on the bottom of the stone, so that repositioning the prosthesis on the articulator to check the bite of the prostheses with a model of the patient's other jaw is inaccurate. Such a procedure sometimes caused defective castings which could not be used, and the dental patient had to be called back in to the dentist's office for another impression, causing additional work for the dentist, and delay for the patient.

An alternate solution to the grinding process is to break away the plaster from the stone model which holds the too-tall wax model of the prosthesis. The stone model is then reset in plaster in an oversize Giant Varsity flask. However, most dental labs & doctors do not have the Giant Varsity flask or the required associated equipment. In addition, the process requires the extra step of replastering the stone model.

Applicant's flask expander simply adds the necessary height to the flask, and the molding process can be completed without the time consuming, and sometimes unsuccessful, grinding step or the expensive oversize flask and related accessories. The flask expander requires no alteration or modification of the standard dental flask, and merely sandwiches in between the existing flask base and body. The flask expander can be made in a number of sizes, one of which can be used for every situation where the standard Hanau flask is not tall enough.

Although the problem of providing enough height in the Hanau flask has existed since the flask was introduced, applicant's expander device is the first simple solution offered for those cases in which the total height of the flask is insufficient to provide clearance for a particularly tall prosthesis model. The dental prosthesis manufacturer may still use the standard Hanau flask with the simple addition of applicant's expander device to gain the required added height for the molding process.

BRIEF DESCRIPTION OF THE DRAWINGS

FIG. 1 of the drawings is an exploded, perspective view with some parts broken away of the parts of a dental flask showing the flask expander in relation to the conventional parts of the dental flask;

FIG. 2. is a top plan view of the expander shown in FIG. 1;

FIG. 3 is a sectional view taken on line 3-3 of FIG. 2;

FIG. 4 is a schematic side view showing a wax upper jaw denture model with replacement teeth in place in partially poured stone and plaster in the assembled base and body member with the wax denture model extending above the height of the body member;

FIG. 5 is a side plan view with parts broken away, showing the body of the flask fitted on top of the flask expander, and the lid in place, with the upper jaw wax denture model and replacement teeth shown after the remaining stone has been poured;

DESCRIPTION OF THE PREFERRED EMBODIMENT

Figure 6:
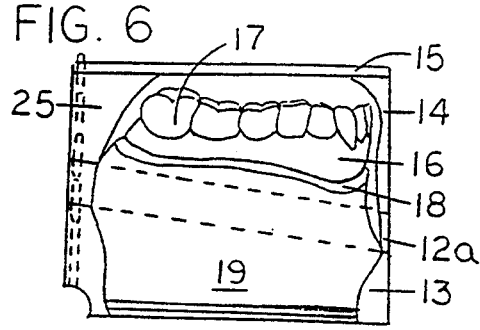
FIG. 6 is similar to FIG. 5, but showing a lower jaw wax denture model in place, with a lower jaw expander shown in phantom.

FIG. 1 shows a conventional Hanau flask 11 for making an upper jaw dental prosthesis with the expander 12 shown disposed between the base 13 and the body 14. Over the body 14 is a lid 15. When all of the parts are pushed together, they form a chamber which encloses the denture model 16 anchored in stone model 18 and plaster 19 during the molding and curing of the prothesis.

FIG. 4 of the drawings shows a wax denture model 16 with replacement teeth 17 mounted in stone model 18 and partially poured plaster 19. It can be seen that the replacement teeth 17 are too high to be enclosed by the lid 15 with enough stone around the upper ends of the teeth 17 to hold them in fixed relationship when the wax dental bridge model 16 is melted out.

The usual method of saving the overly high dental bridge model 16 would be to grind down the base of the stone model 18 to gain the needed height in the flask 11. This has the effect of modifying the guide marks 20 (FIGS. 7-9) formed in the base of the stone model 18, and thereby modifies the precision of the repositioning of prosthesis 23 in plaster mount 21 (FIG. 10), which is mounted on mounting plate 22 in articulator 24. Grinding guide marks 20 throws off the precise matching of the negative guide marks 20 to the corresponding guide protuberances 26, and, therefore, greatly increasing the required bite adjustment by the technician. Guide marks 20 were formed in the base of the stone model 18 when the denture model 16 was first mounted in the plaster mount 21 on the articulator 24.

The articulator 24 (FIG. 10) is a hinged device used to accurately set the synthetic teeth 17 in the wax denture model 16 prior to the investment molding of the prosthesis 23. A model of the dental patient's opposing jaw and teeth (not shown) is set in the opposing half of the articulator 24, and the wax model 16 of the prosthesis 23 is carefully positioned in the opposite half of the articulator 24. The wax denture model 16 is mounted on the stone model 18 which has the guide marks 20 formed in its base. When the stone model 18 is positioned in wet plaster in the articulator 24, the guide marks 20 are filled in by complementary positive guide protuberances 26 in the adjacent wet plaster, which then sets and provides a precise reference for positioning the completed dental prosthesis 23 in the articulator 24 to adjust the bite. The plaster mount 21 and the opposing jaw model (not shown) remain on the articulator 24 when the wax denture model 16 mounted on the stone model 18 is removed for the molding process, so the relationship between the new dental prosthesis 23 and the model of the patient's opposing jaw and teeth should be precisely the same as it was for the wax denture model 16 for accurate bite adjustment of the dental prosthesis 23 in the laboratory.

When the guide marks 20 are ground down in an attempt to save the original, overly high, wax model 16, the refitting of the new prosthesis 23 onto the plaster mount 21 which is set on mounting plate 22 of the articulator 24 becomes imprecise. This usually causes considerably more grinding and bite adjustment by the dentist with the patient in the dental chair. In some cases, the prosthesis is beyond repair, and must be discarded. The whole time consuming procedure must be re-initiated from the beginning.

Figure 11:
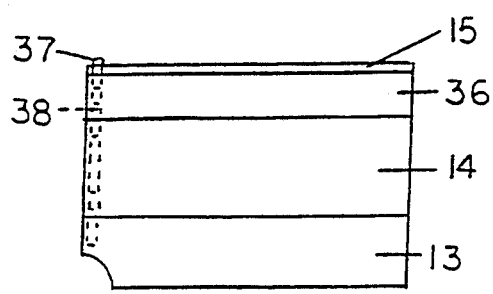
FIG. 11 is a side view showing another embodiment of the expander in which the expander is disposed above the body of the flask.

As seen in FIG. 5, 6 and 11 the very simple insertion of the flask expander 12, 12a or 36 between the body 14 and the base 13 of the standard Hanau dental flask 10 (FIGS. 5 and 6), or between the body 14 and the lid 15 (FIG. 11) provides the necessary added height to the body 14 so that the molding process can be completed in the conventional manner. The expander 12 provides the added height necessary to mold stone 25 above and around the upper ends of the teeth 17 so that the teeth 17 can be removed and held in fixed relationship to each other and to the lower mold when the wax denture model 16 is melted out, and later replaced by liquid methyl methacrylate of the dental prosthesis 23. The liquid methyl methacrylate fills in the void left by the lost wax, cures and fuses to the lower ends of the teeth 17 which are held in correct position by stone 25 in the top part of the flask 10.

The guide marks 20 in the base of the stone model 18 are undisturbed by the molding process. The plaster 19 is removed from the bottom of stone model 18, which now supports the new prosthesis 23. The stone model 18 with newly formed prosthesis 23 mounted thereon is then remounted on the articulator 24. The guide marks 20 register precisely with the complementary protuberances 26 in the original plaster mount 21.

This precise positioning of the new prosthesis 23 in the articulator 24 greatly facilitates accurate bite adjustment of the prosthesis 23 in the dental lab. This precise positioning is not possible when the guide marks 20 are ground down in an attempt to rescue an overly tall wax model 16. The use of the flask expander 12, 12a or 36 makes it possible to save high denture models 16 without grinding away the protuberances 26. With the accurate placement of the dental prosthesis 23 in the articulator 24, less adjustment is then necessary by the dentist with the patient in the dental chair, resulting in a substantial time saving and economy for everyone.

The expander 12 is best seen in FIGS. 1–3. Expander 12 includes an annular member 27 having a pair of downwardly descending pilot pins 28. The pilot pins 28 fit into the pilot pin openings 29 on the base 13. A pair of pilot pin openings 30 are disposed directly above the pilot pins 28 for receiving pilot pins 31 which extend downwardly from the body 14, as best seen in FIG. 1.

It is important that the expander 12 have exactly the same contour and dimensions on its top surface 32 and bottom surface 33, so that expander 12 can mate accurately with the lower surface 34 of the body 14 and upper surface 35 of the base 13 of the flask 11. The parts of the flask 11 can then be easily disassembled between the steps of the manufacture of the dental prosthesis 23.

FIG. 6 of the drawings shows the somewhat angular contour of expander 12a, required to make a lower jaw prosthesis. The function of the lower jaw expander 12a is substantially the same as described for upper jaw expander 12.

Figure 7:
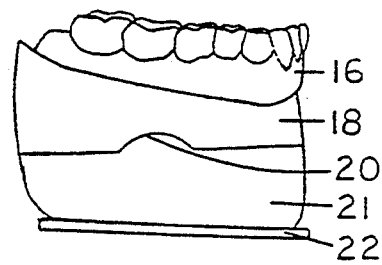
FIG. 7 is a side view of a wax denture stone model with some parts broken away showing the stone model having a guide mark mounted on the articulator plaster mount with the guide marks matched up with the complementary plaster guide mark.
Figure 8:
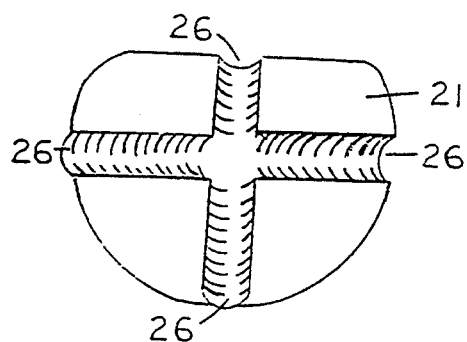
FIG. 8 is a top plan view of the articulator plaster mount shown in FIG. 7 to show the cross-shaped, positive guide marks formed in the articulator plaster mount.
Figure 9:
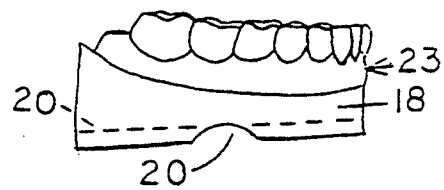
FIG. 9 is a side plan view of just the stone model carrying the finished denture having the negative guide shown in FIG. 7, to show the negative guide which exactly mates with the positive guide marks shown in FIG. 8.

FIGS. 7–9 of the drawings illustrate why it is important to avoid grinding the bottom of the stone model 18 to attempt to make an overly high wax model 16 fit ia a flask 11. If guide marks 20 are ground down, the precise fit with protuberances 26 on the top of the plaster mount 21 (FIG. 8) will be destroyed. Retention of the precise fit of the prosthesis 23 is made possible by using the expander 12, 12a or 36 in the flask 11 so that additional height is gained without the need for grinding the bottom of the stone model 18.

Figure 10:
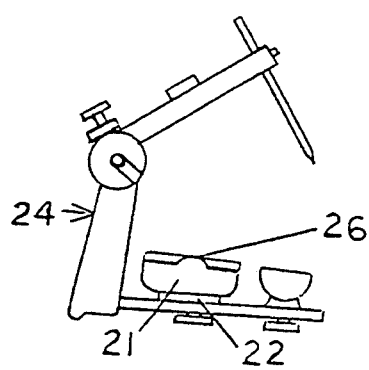
FIG. 10 is a schematic side plan view of an articulator showing the plaster mount in place, ready to receive the stone model carrying the finished denture so that bite adjustment can be made.

FIG. 10 of the drawings shows the plaster mount 21 with the complementary protuberances 26 on which the negative guide marks 20 in stone model 18 will be replaced, now with the prosthesis 23 made from the wax model 16. The mounting plate 22 firmly secures the plaster mount 21 to the articulator 24, and a model of the patient's opposing jaw (not shown) is firmly mounted on the movable arm for precise bite adjustment in the dental laboratory.

Figure 12:
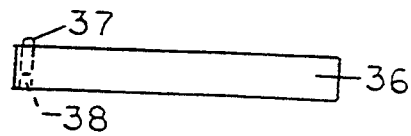
FIG. 12 is a side view of the modified expander shown in FIG. 11.

FIGS. 11 and 12 of the drawings show another embodiment of the expander, which is adapted to fit between the body 14 and the lid 15. Expander 36 is generally similar to the expanders 12 and 12a, except that it has upwardly projecting pilot pins 37 which register with openings 15a in the lid 15. Openings 38 on the underside of the pilot pins 37 receive upwardly extending pilot pins 31a of the body 14. The expander 36 functions in a manner similar to the expanders 12 and 12a to provide sufficient added height to salvage overly high wax models 16 without grinding the guide marks 20 of the stone model 18.

The dental flask expander of the invention makes possible the use of wax dental models which are otherwise too tall for assembly in a conventional Hanau dental flask. Insertion of the flask expander between the base and the body, or the body and the lid of a conventional Hanau flask provides the required added height to proceed with the casting steps without destroying the plaster portion of the wax model cast, and without grinding down on the guide marks on the bottom of the stone of the wax model cast. Because the negative guide marks on the bottom of the stone are not disturbed, greater accuracy in repositioning the finished prosthesis in the articulator for bite adjustment is attained. As a direct result, the dentist and patient need to do less bite adjusting in the dentist's chair to get a good fit. The extra time necessary when new impressions would be needed is also avoided.

An important requirement of the expander is that its inner surface must provide a smooth transition between the base and the body, or the body and the lid, so that no ridges or irregularities are formed in the surface of the stone model.

What is claimed is:

1. A flask expander for a three-part flask having a base, a body and a lid which together define a contoured molding chamber in which a wax model is placed for investment molding of a prosthesis by the lost wax process, said expander comprising:

an annular member having a central opening conforming to a generally transverse section of the contoured molding chamber, said annular member being adapted to be disposed between two of the parts of the dental flask for increasing the height of the molding chamber to accommodate an overly tall wax model, said annular member having a inner surface which provides a smooth transition between the two parts between which the expander is disposed so that no ridges or irregularities are formed in the stone model, said expander having a vertical height less than the height of either the base or the body of the flask, and greater than the vertical height of the lid;

pin members protruding from the annular member adapted to fit in complementary pin receiving openings of the first adjacent part of the three-part flask; and pin receiving openings of the opposite side of the annular member adapted to receive pin members of a second adjacent part of the three-part flask, whereby a four-part flask having a molding chamber of increased height equal to the height of the expander is defined.

2. The flask expander of claim 1, in which the body of the flask has a pair of downwardly extending pilot pins, and the base has a pair of complementary pilot pin receiving openings on its upper, open surface, the flask expander has a pair of downwardly extending pilot pins substantially identical to the downwardly extending pilot pins of the body adapted to be received in the complementary pilot pin receiving openings in the base, said flask expander also having complementary pilot pin openings on its upper surface which are substantially identical to the pilot pin receiving openings on the upper surface of the base, whereby the expander may be disposed between the base and the body of the flask to increase the height of the molding chamber defined thereby.

3. The flask expander of claim 1, in which the body of the flask has a pair of upwardly extending pilot pins, and the lid has a pair of complementary pilot pin receiving openings for normally receiving the upwardly extending pilot pins of the body, said expander having upwardly extending pilot pins on its upper surface which are substantially identical to the upwardly extending pilot pin on the flask body, and said expander having downwardly extending openings corresponding in depth and position to the pilot pin receiving openings of the flask lid, whereby the expander may be inserted between the body and the lid of the flask to increase the height of the molding chamber defined thereby.

4. The flask expander of claim 1, in which the flask parts have generally horizontal top and bottom surfaces when the assembled flask is in an upright position, and said expander has generally horizontal top and bottom surfaces.

5. The flask expander of claim 1, in which the base and the body of the flask have normally opposed surfaces which are contoured to accommodate a lower jaw dental prosthesis, and the expander has complementary top and bottom surfaces which are contoured to fit between the base and the body of the flask to increase the vertical height of the molding chamber.

6. In a method of making a precision prosthesis from liquid methyl methacrylate in a three-part flask defining a molding chamber employing wax/stone models and an articulator having guide marks which form complementary guide marks in the wax/stone model, said wax/stone model being slightly too tall for the molding chamber, the step of inserting a complementary, annular expander member between two of the three parts of the flask to increase the height of the molding chamber enough to accommodate the slightly too tall wax/stone model, and thereby avoid grinding down the base of the wax/stone model to fit into the three-part flask thereby avoiding obliteration of the guide marks formed in the wax/stone model which are used to precisely reposition the stone model in the articulator to facilitate accurate bite adjustment, even though the wax/stone model was slightly too tall for a conventional three-part flask.

7. The method of claim 6, in which the three-part flask includes a base, a body and a lid, and the expander is inserted between the base and the body.

8. The method of claim 6, in which the three-part flask includes a base, a body and a lid, and the expander member is inserted between the body and the lid.

* * * * *